United States Patent
Park et al.

(10) Patent No.: US 9,817,473 B2
(45) Date of Patent: Nov. 14, 2017

(54) PORTABLE DEVICE AND METHOD OF CONTROLLING THEREFOR

(71) Applicant: LG ELECTRONICS INC., Seoul (KR)

(72) Inventors: Sihwa Park, Seoul (KR); Juhwan Lee, Seoul (KR); Doyoung Lee, Seoul (KR); Sinae Chun, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 148 days.

(21) Appl. No.: 14/634,141

(22) Filed: Feb. 27, 2015

(65) Prior Publication Data

US 2016/0187965 A1  Jun. 30, 2016

(30) Foreign Application Priority Data

Dec. 30, 2014 (KR) .......................... 10-2014-0193823

(51) Int. Cl.

| G06F 3/01 | (2006.01) |
|---|---|
| G06F 1/16 | (2006.01) |
| G01C 21/00 | (2006.01) |
| A61B 5/00 | (2006.01) |
| A61B 5/11 | (2006.01) |
| A61B 5/117 | (2016.01) |

(52) U.S. Cl.
CPC .............. G06F 3/011 (2013.01); G01C 21/00 (2013.01); G06F 1/163 (2013.01); A61B 5/117 (2013.01); A61B 5/1112 (2013.01); A61B 5/6807 (2013.01); A61B 5/6829 (2013.01)

(58) Field of Classification Search
CPC ....................................................... G06F 3/011
See application file for complete search history.

(56) References Cited

U.S. PATENT DOCUMENTS

| 6,452,544 B1 | 9/2002 | Hakala et al. |
|---|---|---|
| 7,911,339 B2 | 3/2011 | Vock et al. |
| 8,280,681 B2 | 10/2012 | Vock et al. |
| 8,329,284 B2 | 12/2012 | Seitz |
| 8,526,677 B1 | 9/2013 | Crichton et al. |
| 2003/0080869 A1* | 5/2003 | Pellet ..................... G01C 21/20 340/573.1 |
| 2007/0006489 A1 | 1/2007 | Case, Jr. et al. |
| 2007/0190494 A1* | 8/2007 | Rosenberg .............. A63F 13/12 434/11 |

(Continued)

FOREIGN PATENT DOCUMENTS

| KR | 10-2007-0092908 A | 9/2007 |
|---|---|---|
| WO | WO 2007/001724 A1 | 1/2007 |
| WO | WO 2013/061856 A1 | 5/2013 |

*Primary Examiner* — Ariel Balaoing
(74) *Attorney, Agent, or Firm* — Birch, Stewart, Kolasch & Birch, LLP

(57) ABSTRACT

A method of controlling a portable device according to one embodiment of the present specification may include the steps of displaying a first application including a first object and a second object, receiving a first triggering signal indicating that a front direction of the foot wearable device corresponds to a first direction from the foot wearable device, detecting a front direction of the portable device corresponding to a second direction, displaying the first object based on the first direction and displaying the second object based on the second direction.

14 Claims, 15 Drawing Sheets

(56) References Cited

U.S. PATENT DOCUMENTS

| | | | |
|---|---|---|---|
| 2007/0210930 A1 | 9/2007 | Pyo et al. | |
| 2007/0231778 A1* | 10/2007 | Kim | A63B 69/00 |
| | | | 434/250 |
| 2008/0040951 A1 | 2/2008 | Kates | |
| 2010/0082288 A1 | 4/2010 | Cattin et al. | |
| 2013/0222270 A1* | 8/2013 | Winkler | H04M 1/0233 |
| | | | 345/173 |
| 2013/0231889 A1* | 9/2013 | Hrybyk | G01C 21/20 |
| | | | 702/141 |
| 2014/0062703 A1* | 3/2014 | Purks | A61B 5/1122 |
| | | | 340/573.1 |
| 2014/0278067 A1* | 9/2014 | Gordon | G01C 21/367 |
| | | | 701/457 |
| 2014/0286534 A1 | 9/2014 | Haverinen | |
| 2015/0378662 A1* | 12/2015 | Wan | G06F 3/1423 |
| | | | 345/156 |
| 2016/0036953 A1* | 2/2016 | Lee | H04M 1/576 |
| | | | 455/426.1 |
| 2016/0187965 A1* | 6/2016 | Park | G06F 3/011 |
| | | | 345/156 |

* cited by examiner

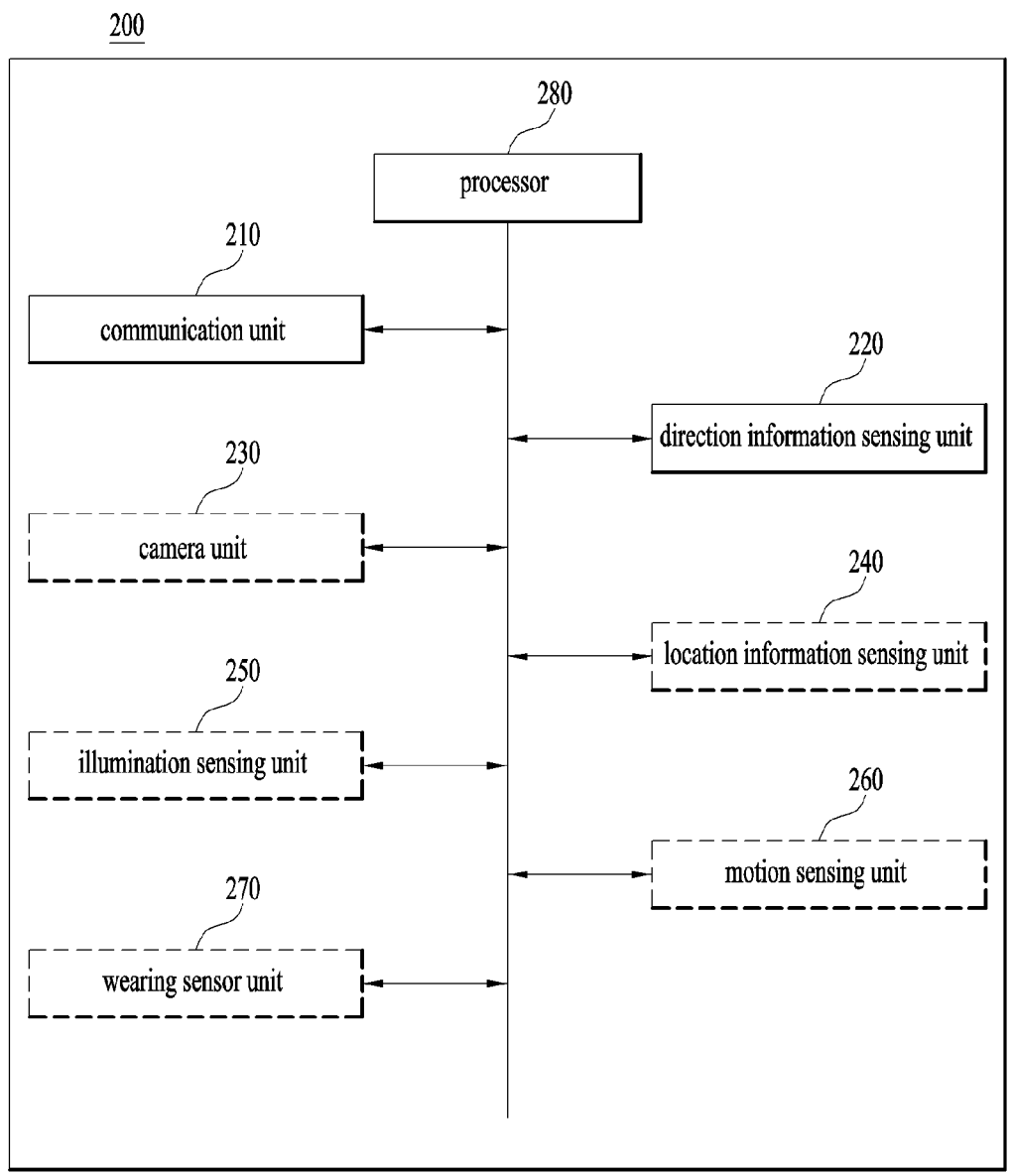

FIG. 3a
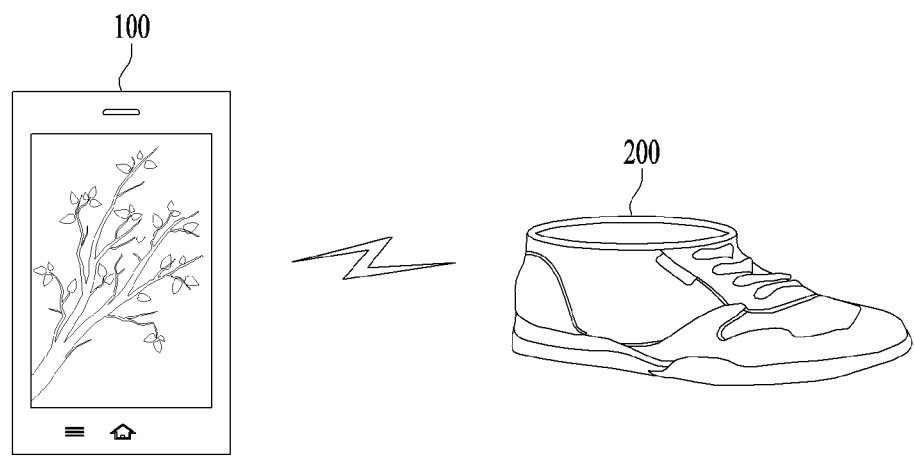
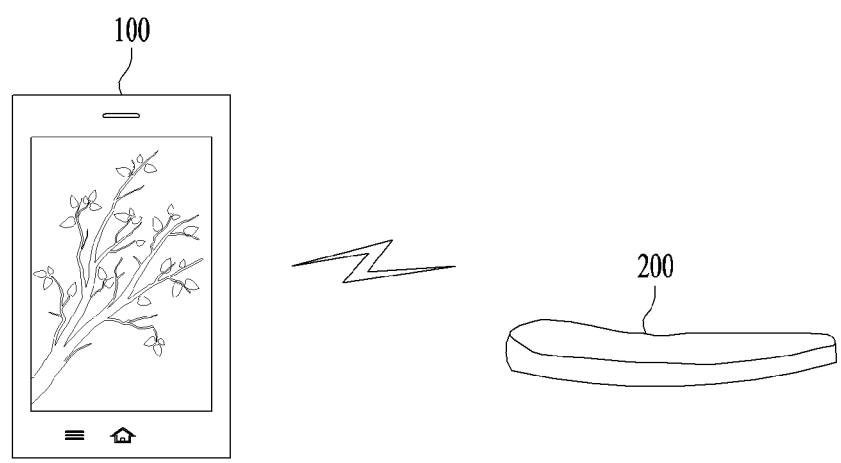

FIG. 3b
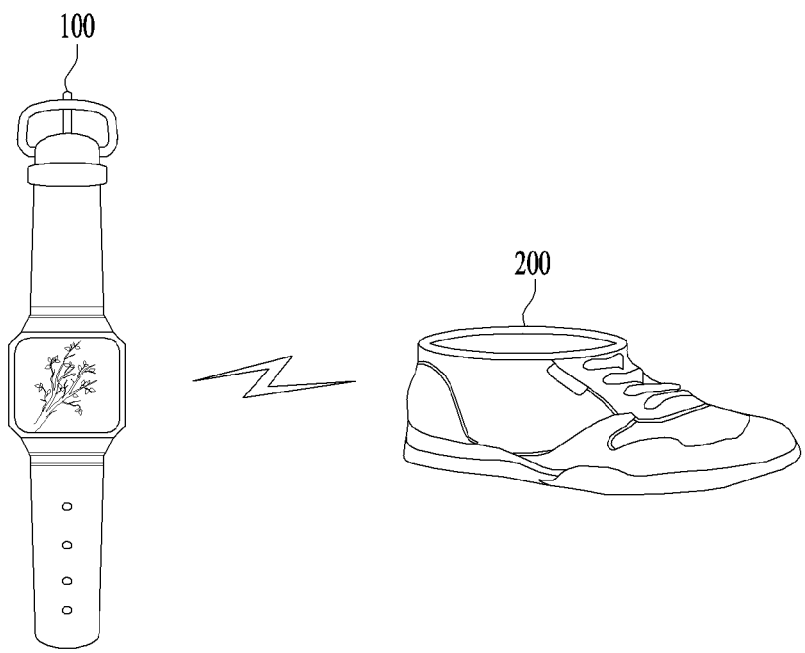
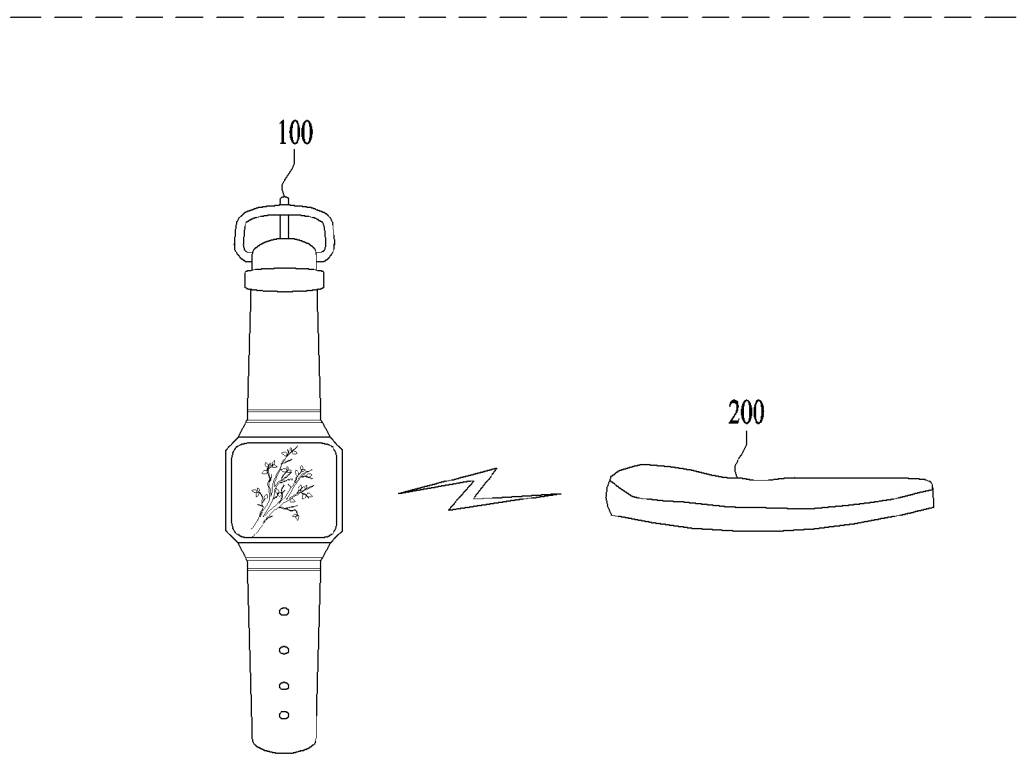

FIG. 6
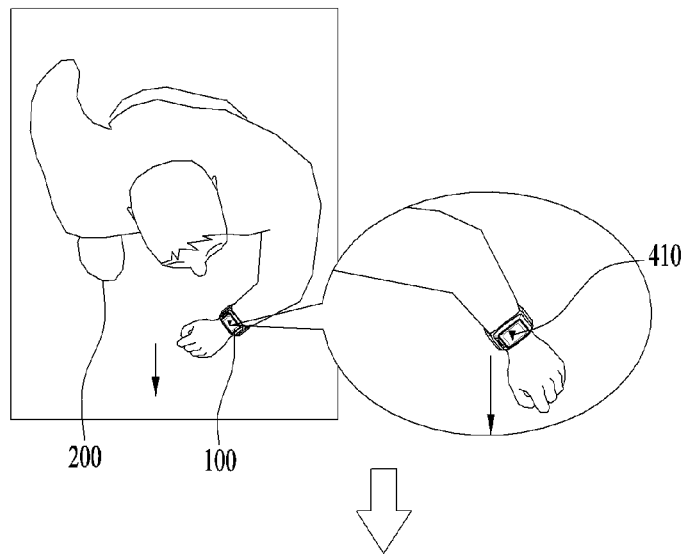
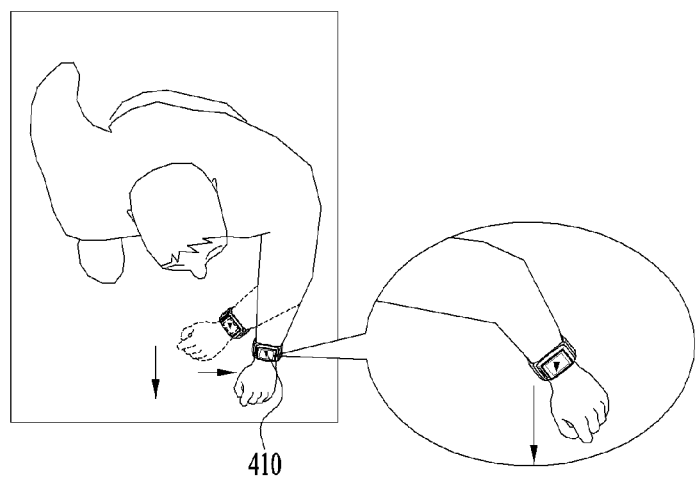
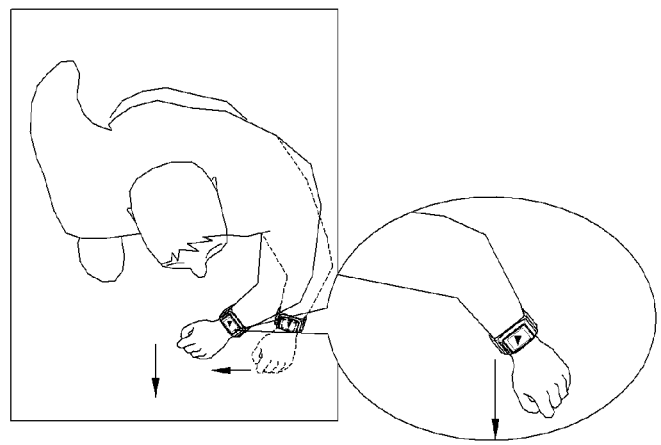

FIG. 7a
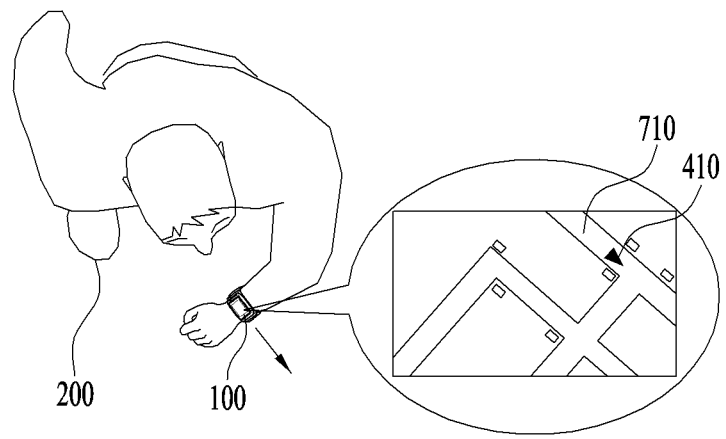
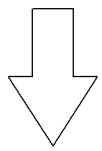
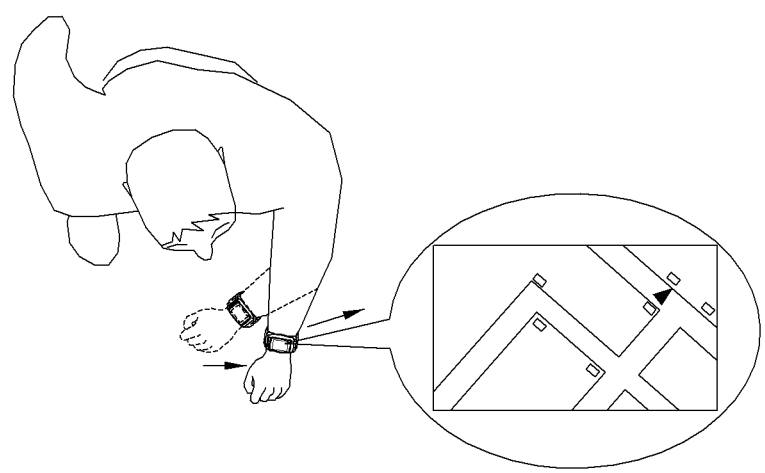

FIG. 7b
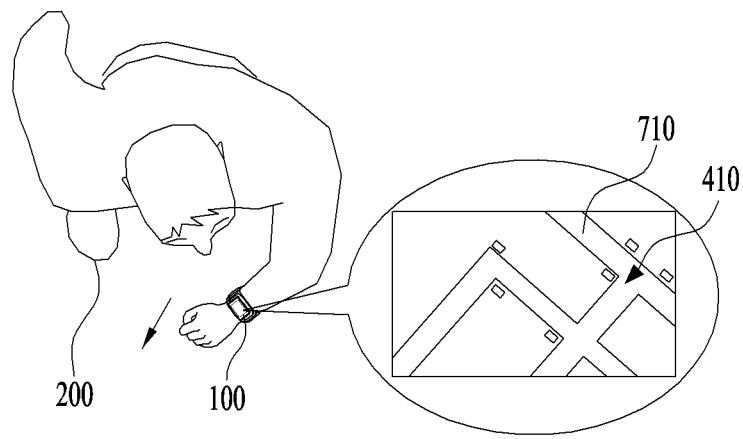
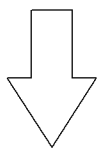
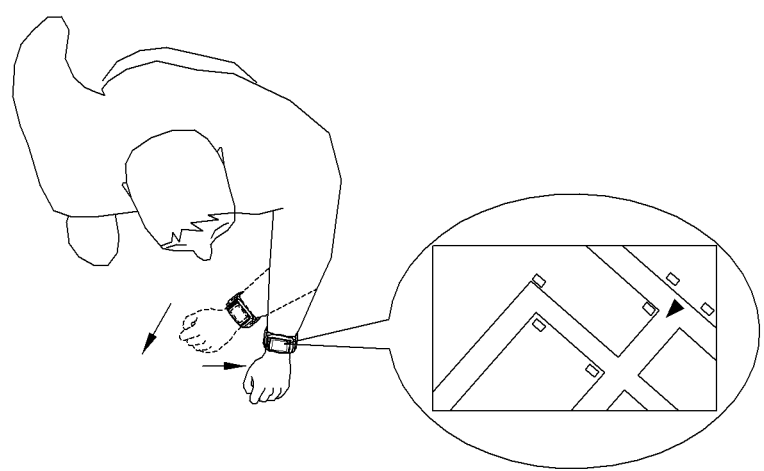

FIG. 8
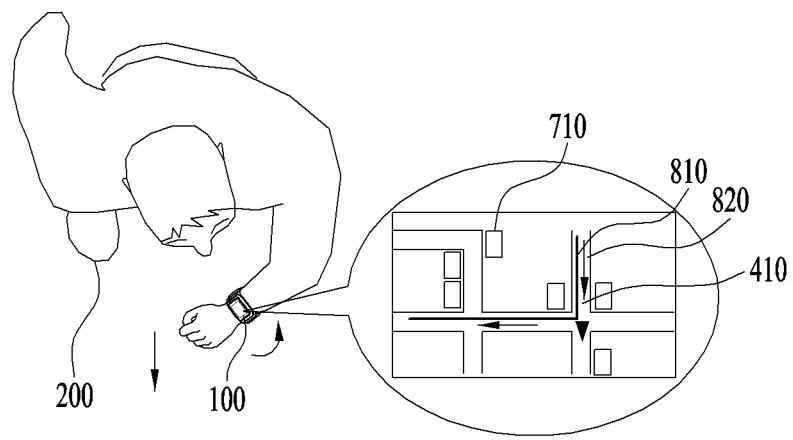
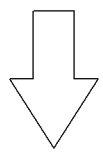
You are moving in a direction different from a path
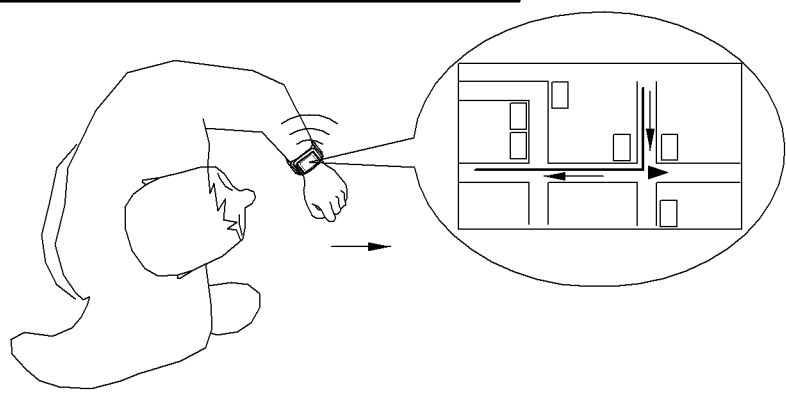

FIG. 11
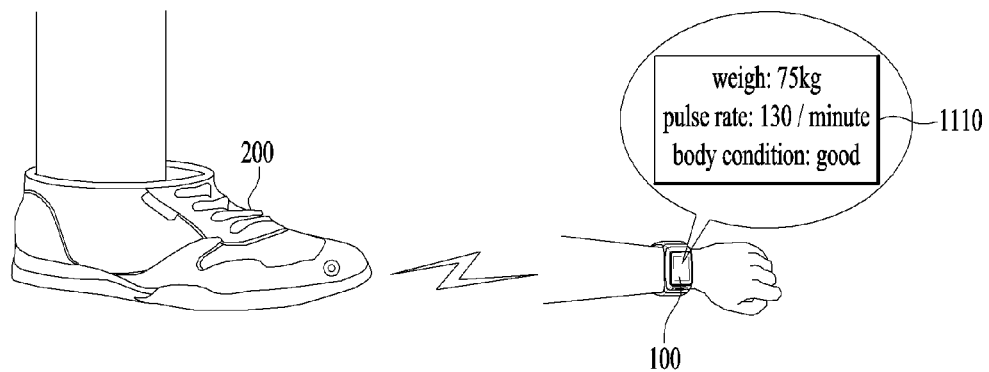
FIG. 12a
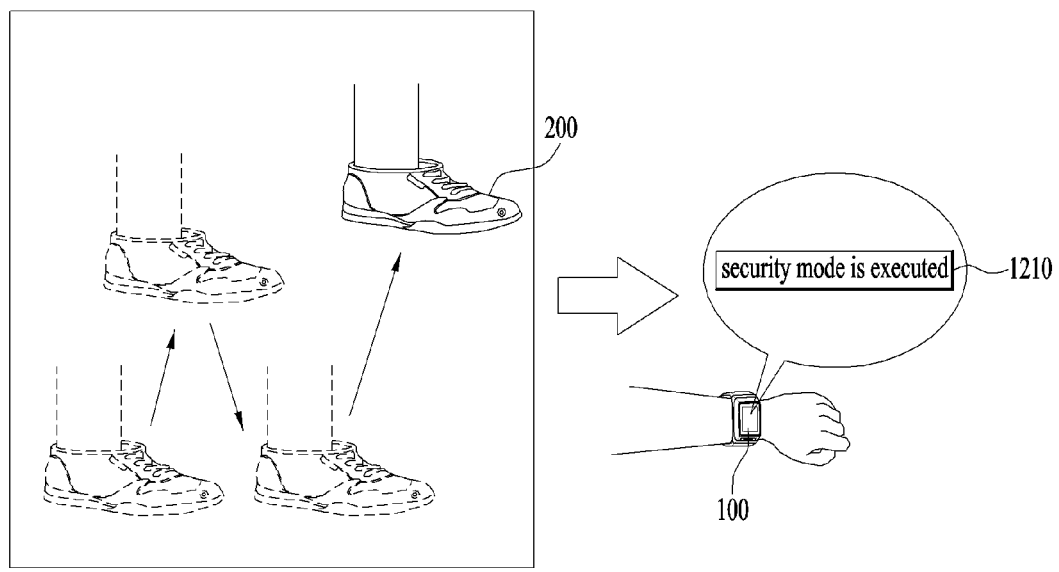
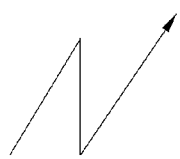

PORTABLE DEVICE AND METHOD OF CONTROLLING THEREFOR

This application claims the benefit of the Korean Patent Application No. 10-2014-0193823, filed on Dec. 30, 2014, which is hereby incorporated by reference as if fully set forth herein.

BACKGROUND OF THE INVENTION

Field of the Invention

The present specification relates to a portable device and a method of controlling therefor.

Discussion of the Related Art

Recently, a use of a portable device is increasing. And, a use of a wearable device, which is used in a manner of being worn on a body of a user, is increasing. In this case, the portable device and the wearable device may be used in a manner of being interlocked with each other. In particular, the portable device and the wearable device may share information with each other via a communication unit. In this case, the wearable device may correspond to a device capable of being worn on a body of a user. In this case, as an example, the wearable device may correspond to a device capable of being worn on a foot of the user. In this case, it is required to have a method of using the wearable device capable of being worn on the foot of the user by interlocking with the portable device.

SUMMARY OF THE INVENTION

Accordingly, the present specification is directed to an apparatus and method thereof that substantially obviate one or more problems due to limitations and disadvantages of the related art.

An object of the present specification is to provide a portable device and a method of controlling therefor.

Another object of the present specification is to provide a portable device and a system including a foot wearable device.

Another object of the present specification is to provide a method of displaying an application based on a front direction of a portable device and a front direction of a foot wearable device.

Another object of the present specification is to provide a method for a portable device to display a first object included in a first application based on a front direction of a foot wearable device.

Another object of the present specification is to provide a method for a portable device to display a second object included in a first application based on a front direction of the portable device.

Another object of the present specification is to provide a method for a portable device to provide path information based on current location information of the portable device.

Another object of the present specification is to provide a method for a portable device to provide a method of controlling an operation of the portable device based on information on whether a foot wearable device is worn.

Another object of the present specification is to provide a method for a foot wearable device to control an operation based on user information in a system including the foot wearable device.

The other object of the present specification is to provide a method of controlling operations of a plurality of devices based on information on whether a foot wearable device is worn in a system including the foot wearable device.

Additional advantages, objects, and features of the invention will be set forth in part in the description which follows and in part will become apparent to those having ordinary skill in the art upon examination of the following or may be learned from practice of the invention. The objectives and other advantages of the invention may be realized and attained by the structure particularly pointed out in the written description and claims hereof as well as the appended drawings.

A portable device may be provided according to one embodiment of the present specification. In this case, the portable device may include a display unit configured to display visual information, a direction information sensing unit configured to detect direction information of the portable device, a communication unit configured to receive information from a foot wearable device and a processor configured to control the display unit, the direction information sensing unit and the communication unit. In this case, the processor may display a first application including a first object and a second object, receive a first triggering signal indicating that a front direction of the foot wearable device corresponds to a first direction from the foot wearable device, if a front direction of the portable device is detected as a second direction, display the first object based on the first direction and display the second object based on the second direction.

A method of controlling a portable device according to one embodiment of the present specification may include the steps of displaying a first application including a first object and a second object, receiving a first triggering signal indicating that a front direction of the foot wearable device corresponds to a first direction from the foot wearable device, detecting a front direction of the portable device corresponding to a second direction, displaying the first object based on the first direction and displaying the second object based on the second direction.

According to the present specification, it is able to provide a portable device and a method of controlling therefor.

According to the present specification, it is able to provide a portable device and a system including a foot wearable device.

According to the present specification, it is able to provide a method of displaying an application based on a front direction of a portable device and a front direction of a foot wearable device.

According to the present specification, a portable device may display a first object included in a first application based on a front direction of a foot wearable device.

According to the present specification, a portable device may display a second object included in a first application based on a front direction of the portable device.

According to the present specification, a portable device may provide path information based on current location information of the portable device.

According to the present specification, a portable device may control an operation of the portable device based on information on whether a foot wearable device is worn.

According to the present specification, a foot wearable device may control an operation based on user information in a system including the foot wearable device.

According to the present specification, it is able to control operations of a plurality of devices based on information on whether a foot wearable device is worn in a system including the foot wearable device.

It is to be understood that both the foregoing general description and the following detailed description of the present specification are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this application, illustrate embodiment(s) of the invention and together with the description serve to explain the principle of the invention.

FIG. 2 is a block diagram for a foot wearable device according to one embodiment of the present specification;

FIGS. 3a and 3b are diagrams for a system including a wearable device according to one embodiment of the present specification;

FIG. 6 is a diagram of a method for a portable device to display a first object based on a front direction of a foot wearable device according to one embodiment of the present specification;

FIGS. 7a and 7b are diagrams of a method for a portable device to display a first application including a first object and a second object according to one embodiment of the present specification;

FIG. 8 is a diagram of a method for a portable device to provide feedback based on path information according to one embodiment of the present specification;

FIG. 11 is a diagram for a method of interlocking a foot wearable device and a portable device in a system including a wearable device according to one embodiment of the present specification;

FIGS. 12a and 12b are diagrams for a method of interlocking a foot wearable device and a portable device in a system including a wearable device according to one embodiment of the present specification;

DETAILED DESCRIPTION OF THE INVENTION

While embodiments have been described in detail with reference to the attached drawings and contents written on the drawings, the scope of claims may be non-restricted or non-limited by the embodiments.

Although terminologies used in the present specification are selected from general terminologies used currently and widely in consideration of functions, they may be changed in accordance with intentions of technicians engaged in the corresponding fields, customs, advents of new technologies and the like. Occasionally, some terminologies may be arbitrarily selected by the applicant(s). In this case, the meanings of the arbitrarily selected terminologies shall be described in the corresponding part of the detailed description of the specification. Therefore, terminologies used in the present specification need to be construed based on the substantial meanings of the corresponding terminologies and the overall matters disclosed in the present specification rather than construed as simple names of the terminologies.

Moreover, a terminology, each of which includes such an ordinal number as first, second and the like, may be used to describe various components. In doing so, the various components should be non-limited by the corresponding terminologies, respectively. The terminologies are only used for the purpose of discriminating one component from other components. For instance, a first component may be named a second component while coming within the scope of the appended claims and their equivalents. Similarly, the second component may be named the first component.

In the present application, such a terminology as 'comprise', 'include' and the like should be construed not as necessarily excluding various components or steps written in the present specification but as including the components or steps in part or further including additional components or steps. And, such a terminology as 'unit' written in the present specification indicates a unit processing at least one function or an operation and may be implemented by hardware, software or a combination thereof.

Figure 1:
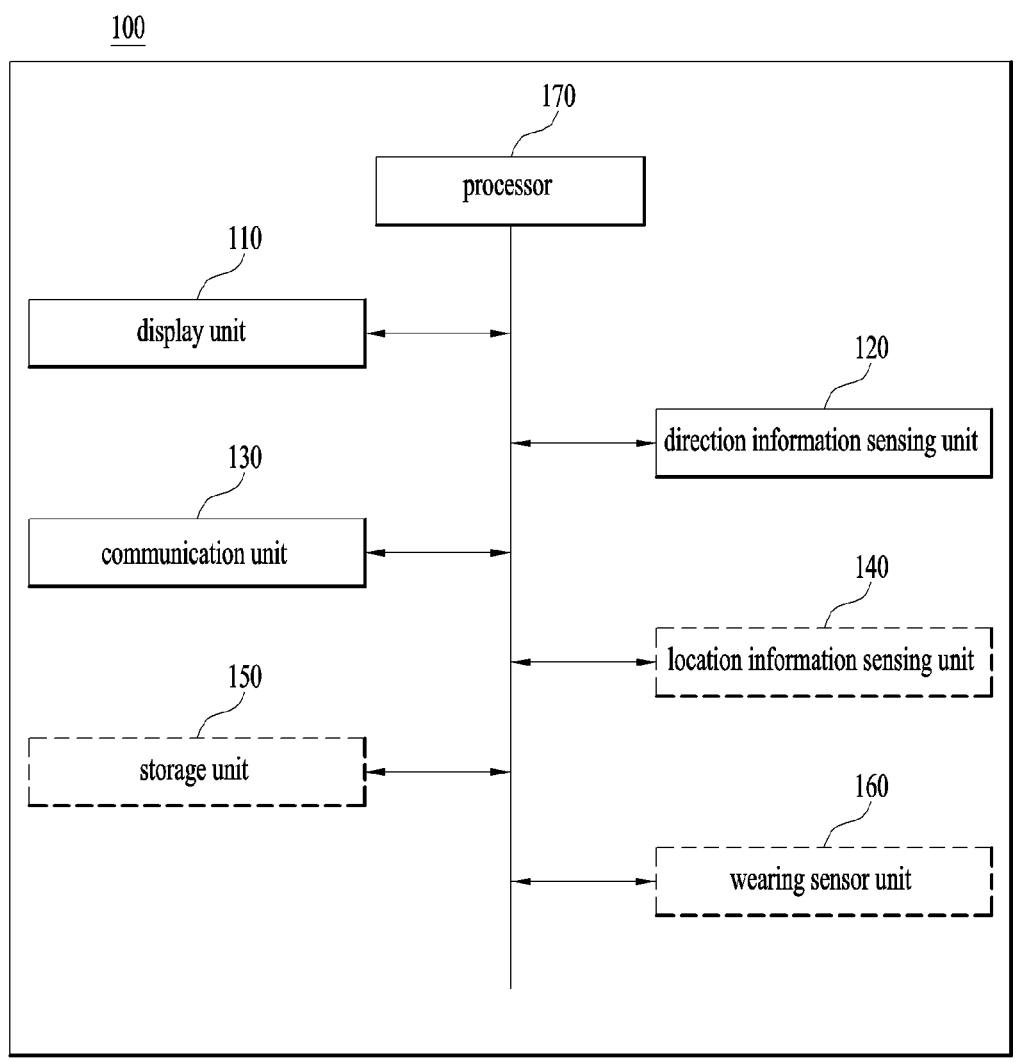
FIG. 1 is a block diagram for a portable device according to one embodiment of the present specification.

FIG. 1 is a block diagram for a portable device according to one embodiment of the present specification. A portable device 100 may correspond to a device displaying visual information and performing communication with a different device. In this case, as an example, the portable device 100 may corresponds to a smartphone, a smart pad, a notebook or the like. As a different example, the portable device 100 may correspond to a wearable device capable of being worn by a user. As an example, the portable device 100 may correspond to a smart watch, a HMD or the like. In particular, the portable device 100 may correspond to a device providing visual information to a user and performing communication with a different device, by which the present specification may be non-limited.

The portable device 100 may include a display unit 110, a direction information sensing unit 120, a communication unit 130 and a processor 170. And, the portable device 100 may further include a location information sensing unit 140 as an optional configuration. And, the portable device 100 may further include a storage unit 150 as an optional configuration. And, the portable device 100 may further include a wearing sensor unit 160 as an optional configuration. In this case, as an example, each of the units may correspond to a component or a part constructing the portable device 100. In particular, each of the units may correspond to an independent unit housed in the portable device to make the portable device 100 execute a function, by which the present specification may be non-limited.

The display unit 110 may be controlled by the processor 170. In this case, the display unit may display visual information. In this case, the visual information may correspond to information capable of being recognized by vision of a user by including at least one selected from the group consisting of a still image, a video and a text in the information. And, as an example, if the portable device 100 corresponds to a wearable device, the visual image may correspond to a virtual image. In particular, the visual information corresponds to information capable of being recognized by vision of a user, by which the present specification may be non-limited. In particular, the display unit 110 may correspond to a unit providing visual information to a user, by which the present specification may be non-limited.

And, the direction information sensing unit 120 may be controlled by the processor 170. In this case, as an example, the direction information sensing unit 120 may detect a front direction of the portable device 100. In this case, as an example, the front direction of the portable device 100 may correspond to a direction in which visual information is displayed. More specifically, the processor 170 may display the visual information based on the front direction of the portable device 100. As an example, the processor 170 may display the visual information in a portrait mode or a landscape mode. In this case, the portrait mode may correspond to a state that the portable device 100 stands. In this case, as an example, the front direction of the portable device 100 may correspond to an up direction of the standing portable device. And, the landscape mode may correspond to a state that the portable device 100 is laid. In this case, as an example, the front direction of the portable device 100 may correspond to an up direction in the state that the portable device is laid. In particular, the front direction of the portable device 100 may correspond to a reference direction in which the visual information is displayed. In this case, as an example, the direction information sensing unit 120 may include at least one sensing means selected from the group consisting of a gyro sensor, an acceleration sensor and a gravity sensor. The direction information sensing unit 120 may detect information on the front direction of the portable device 100 and display the visual information using the at least one sensing means. As a different example, the direction information sensing unit 120 may detect the information on the front direction of the portable device 100 at an external of the portable device 100. In this case, the information on the front direction may correspond to a direction at which the front direction of the portable device 100 is heading based on a bearing of a real space. In particular, the direction information sensing unit 120 may detect the reference direction in which the visual information is displayed and the front direction of the portable device detected at the external of the portable device 100. Regarding this, it shall be described later with reference to FIG. 7a.

And, the communication unit 130 may be controlled by the processor 170. In this case, the communication unit 130 performs communication with the portable device 100 or an external device using various protocols and transceives data with the external device using the same. And, the communication unit 130 accesses a network in wired or in wireless and may transceive such a digital data as content and the like with the network. In particular, the communication unit 130 may correspond to a unit configured to exchange data with the external device, by which the present specification may be non-limited.

And, the location information sensing unit 140 may be controlled by the processor 170. In this case, the location information sensing unit 140 may receive location information of the portable device 100. In this case, as an example, the location information sensing unit 140 may include a GPS and may receive the location information of the portable device 100 via a satellite. And, the location information sensing unit 140 may correspond to a unit configured to receive the location information of the portable device 100 using a short distance communication network or base station information. In particular, the location information sensing unit 140 may correspond to a unit configured to receive the location information of the portable device 100, by which the present specification may be non-limited. In this case, the location information sensing unit 140 may periodically receive and obtain the location information of the portable device 100. The portable device 100 may detect a moving path of the portable device using the periodically obtained location information of the portable device 100. In particular, the location information sensing unit 140 may receive location information utilized by the portable device 100, by which the present specification may be non-limited.

And, the storage unit 150 may be controlled by the processor 170. In this case, the storage unit 150 may store such various digital data as a video, audio, an image, an application and the like. And, as an example, the storage unit 150 may store a program used for controlling the processor 170 and may perform a function of temporarily storing input/output data. The storage unit 150 may include various storing spaces such as a flash memory, a RAM (random access memory), an SSD (solid state drive) and the like.

And, the wearing sensor unit 160 may be controlled by the processor 170. In this case, as an example, the portable device may correspond to a wearable device. In this case, the wearing sensor unit 160 may detect whether the portable device 100 is worn. Or, the portable device 100 may detect whether the portable device is worn using a sensor installed in a joint of a buckle of the portable device 100. In particular, the wearing sensor unit 160 may determine whether the portable device 100 is worn by a user using the aforementioned sensor units. At least one or more sensing units among the aforementioned sensing units providing a sensed result, which becomes the basis of the determination, may be called the wearing sensor unit 160 in the present specification.

The processor 170 may correspond to a unit configured to control at least one selected from the group consisting of the display unit 110, the direction information sensing unit 120 and the communication unit 130. And, the processor 170 may further control at least one selected from the group consisting of the location information sensing unit 140, the storage unit 150 and the wearing sensor unit 160. In this case, as an example, the processor 170 may display a first application including a first object and a second object using the display unit 110. In this case, as an example, the first application may correspond to a map application. And, as an example, the portable device 100 may detect current location information of the portable device 100 using the location information sensing unit 140. In this case, the first object may correspond to an object indicating the current location information of the portable device 100. In this case, as an example, the first object may indicate location information and direction information in the first application. Regarding this, it shall be described later with reference to FIG. 7a and FIG. 7b. And, as an example, the second object may correspond to an object indicating information on a real object positioned adjacent to the portable device 100 based on the current location information of the portable device 100. As an example, the second object may correspond to an object corresponding to a plurality of real objects. In particular, the second object may correspond to an object indicating information on a building, a road, a road sign and the like corresponding to a real object in the first application. The second object may correspond to a single or a plurality objects. And, the processor 170 may receive a first triggering signal from a foot wearable device 200 using the communication unit 130. In this case, the first triggering signal may correspond to information indicating that a front direction of the foot wearable device 200 corresponds to a first direction. As an example, the foot wearable device 200 may correspond to a smart shoes or a smart insole. In this case, a direction at which the fore part of the foot wearable device 200 is heading may correspond to the front direction of the foot wearable device 200. Regarding this, it shall be described later with reference to FIG. 2. And, the processor 170 may detect that the front direction of the portable device 100 corresponds to a second direction using the direction information sensing unit 120. In this case, as mentioned in the foregoing description, the front direction may correspond to a reference direction in which visual information is displayed. In this case, the processor 170 may display the first object based on the first direction corresponding to the front direction of the foot wearable device 200. And, the processor 170 may display the second object based on the front direction of the portable device 100. In particular, the first object including direction information may be displayed based on the foot wearable device 200. And, the second object indicating surrounding information may be displayed based on the front direction of the portable device 100. And, the processor 170 may display path information. In this case, the processor 170 may store history information on the path information in the storage unit 150. And, the processor 170 may control whether to execute the first application based on whether the portable device is worn using the wearing sensor unit 160.

And, the aforementioned elements may be respectively included in the portable device 100 as a separate element or may be included in the portable device in a manner of being integrated into at least one or more elements.

FIG. 2 is a block diagram for a foot wearable device according to one embodiment of the present specification. In this case, the foot wearable device 200 may correspond to a device capable of being worn on a foot of a user. As an example, the foot wearable device may correspond to shoes itself. In particular, the shoes may execute an operation by including various units. As a different example, the foot wearable device 200 may correspond to an insole. In particular, the foot wearable device 200 may correspond to a device manufactured by an insole shape going into the shoes. In particular, the foot wearable device 200 may correspond to a device controlled by a foot of a user, by which the present specification may be non-limited.

The foot wearable device 200 may include a communication unit 210, a direction information sensing unit 220 and a processor 280. And, the foot wearable device 200 may further include a camera unit 230 as an optional configuration. And, the foot wearable device 200 may further include location information sensing unit 240 as an optional configuration. And, the foot wearable device 200 may further include an illumination sensing unit 250 as an optional configuration. And, the foot wearable device 200 may further include a motion sensor unit 260 as an optional configuration. And, the foot wearable device 200 may further include a wearing sensor unit 270 as an optional configuration.

In this case, as an example, the communication unit 210 may be controlled by the processor 280. In this case, the communication unit 210 performs communication with the foot wearable device 200 or an external device using various protocols and transceives data using the same. And, the communication unit 210 accesses a network in wired or in wireless and may transceive such a digital data as content and the like with the network. In particular, the communication unit 210 may correspond to a unit configured to exchange data with the external device, by which the present specification may be non-limited.

And, the direction information sensing unit 220 may be controlled by the processor 280. In this case, as an example, the direction information sensing unit 220 may detect a front direction of the foot wearable device 200. In this case, as an example, the front direction may correspond to a direction to which a fore part of the foot wearable device 200 is heading. In particular, the front direction may correspond to a direction to which toes are heading in shoes or an insole. And, as an example, the direction information sensing unit 220 may include at least one sensing means selected from the group consisting of a gyro sensor, an acceleration sensor and a gravity sensor. The direction information sensing unit 220 may detect a moving direction of a user using the at least one or more sensing means.

And, the camera unit 230 may be controlled by the processor 280. In this case, the camera unit 230 may correspond to a unit configured to capture a surrounding image of the foot wearable device 200. In particular, the foot wearable device 200 may capture a surrounding image using the camera unit.

And, the location information sensing unit 240 may be controlled by the processor 280. In this case, the location information sensing unit 240 may receive location information of the foot wearable device 200. In this case, as an example, the location information sensing unit 240 may include a GPS and may receive the location information of the foot wearable device 200 via a satellite. And, the location information sensing unit 240 may correspond to a unit configured to receive the location information of the foot wearable device 200 using a short distance communication network or base station information. In particular, the location information sensing unit 240 may correspond to a unit configured to receive the location information of the foot wearable device 200, by which the present specification may be non-limited.

And, the illumination sensing unit 250 may be controlled by the processor 280. In this case, as an example, the illumination sensing unit 250 may correspond to a unit configured to measure illumination. In particular, the processor 280 may measure illumination in a dark situation using the illumination sensing unit 250. Regarding this, it shall be described later with reference to FIG. 10.

And, the motion sensing unit 260 may be controlled by the processor 280. In this case, as an example, the motion sensing unit 260 may detect movement of a foot of a user. And, the motion sensing unit 260 may deliver information on the movement of the foot of the user to the processor 280. The processor 280 may obtain pattern information based on the information on the detected movement of the foot. Regarding this, it shall be described later with reference to FIG. 12*a*. In this case, the motion sensing unit 260 may include at least one sensing means selected from the group consisting of a gyro sensor, an acceleration sensor and a gravity sensor. In particular, the motion sensing unit 260 may correspond to a unit configured to detect a foot pattern of a user, by which the present specification may be non-limited.

And, the wearing sensor unit 270 may be controlled by the processor 280. In this case, the wearing sensor unit 270 may detect whether the foot wearable device 200 is worn. As an embodiment, the foot wearable device 200 may detect whether the foot wearable device 200 is worn using a proximity sensor. In this case, as an example, the foot wearable device 200 may detect whether the foot wearable device is worn based on predetermined identification information of a user. In particular, the wearing sensor unit 270 may correspond to a unit configured to detect whether the foot wearable device 200 is worn, by which the present specification may be non-limited.

And, the processor 280 may control the communication unit 210 and the direction information sensing unit 220. And, the processor 280 may further control at least one selected from the group consisting of the camera unit 230, the location information sensing unit 240, the illumination sensing unit 250, the motion sensing unit 260 and the wearing sensor unit 270. As an example, the processor 280 may detect that a front direction of the foot wearable device 200 corresponds to a first direction using the direction information sensing unit 220. In this case, the processor 280 may transmit a first triggering signal including information on the first direction to the portable device 100 using the communication unit 210. In this case, the portable device 100 may display a first object based on the received first triggering signal. And, the processor 280 may detect surrounding topographic information using the camera unit 230. In this case, the processor 280 may transmit the surrounding topographic information to the portable device 100 using the communication unit 210. And, the processor 280 may detect location information of the foot wearable device 200 using the location information sensing unit 240. And, the processor 280 may detect illumination of surrounding of the foot wearable device 200 using the illumination sensing unit 250. And, the processor 280 may detect foot movement of a user using the motion sensing unit 260. The processor 280 may execute a security mode by detecting the foot movement of the user. And, the processor 280 may detect whether the foot wearable device is worn using the wearing sensor unit 270. By doing so, the processor 280 may perform synchronization with a different device based on whether the foot wearable device is worn.

FIGS. 3a and 3b are diagrams for a system including a wearable device according to one embodiment of the present specification. A portable device 100 and a foot wearable device 200 may correspond to a single system. More specifically, the portable device 100 may receive front direction information from the foot wearable device 200. In this case, the portable device 100 may display a first object and a second object included in a first application based on the received front direction information. In particular, the portable device 100 and the foot wearable device 200 may operate as a single system in a manner of interworking with each other.

In this case, as an example, referring to FIG. 3a, the portable device may correspond to a smartphone. And, the foot wearable device 200 may correspond to a shoes or an insole. In particular, the foot wearable device 200 may correspond to a device capable of being worn on a foot of a user, by which the present specification may be non-limited.

And, referring to FIG. 3b, the portable device 100 may correspond to a wearable device. As an example, the portable device may correspond to a smart watch. In particular, the portable device 100 may correspond to a device providing visual information in a manner of being worn by a user. The portable device 100 and the foot wearable device 200 may operate as a single system, by which the present specification may be non-limited.

Figure 4:
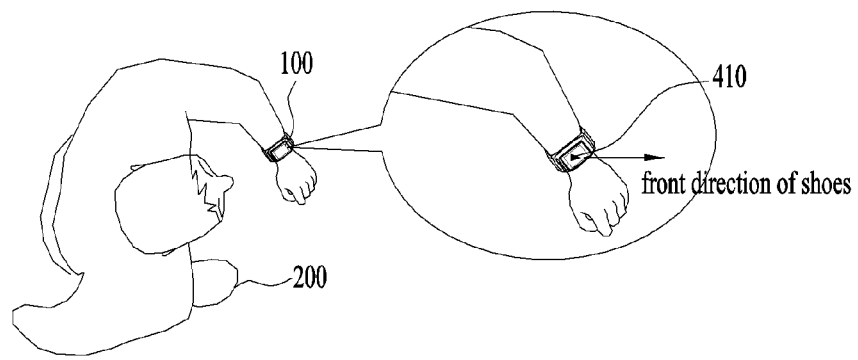
FIG. 4 is a diagram of a method for a portable device to display visual information based on a front direction of a foot wearable device according to one embodiment of the present specification.

FIG. 4 is a diagram of a method for a portable device to display visual information based on a front direction of a foot wearable device according to one embodiment of the present specification. The portable device 100 may receive a first triggering signal from the foot wearable device 200. In this case, the first triggering signal may correspond to a signal indicating that the front direction of the foot wearable device 200 corresponds to a first direction. In this case, the portable device 100 may display a first object 410 based on the first direction. In this case, as an example, the first object 410 may correspond to an arrow shape. In particular, the first object may correspond to an object capable of indicating direction information. In this case, the first object 410 may correspond to an object depending on the front direction of the foot wearable device 200 only. More specifically, a direction of the first object 410 may change only when the front direction of the foot wearable device 200 changes. And, the direction of the first object 410 may be irrespective of whether a front direction of the portable device 100 changes. In particular, the first object 410 may correspond to an object depending on the direction of the foot wearable device 200 only. In this case, since a moving direction of a user and a direction of shoes are identical to each other, the user may easily check the moving direction of the user.

Figure 5:
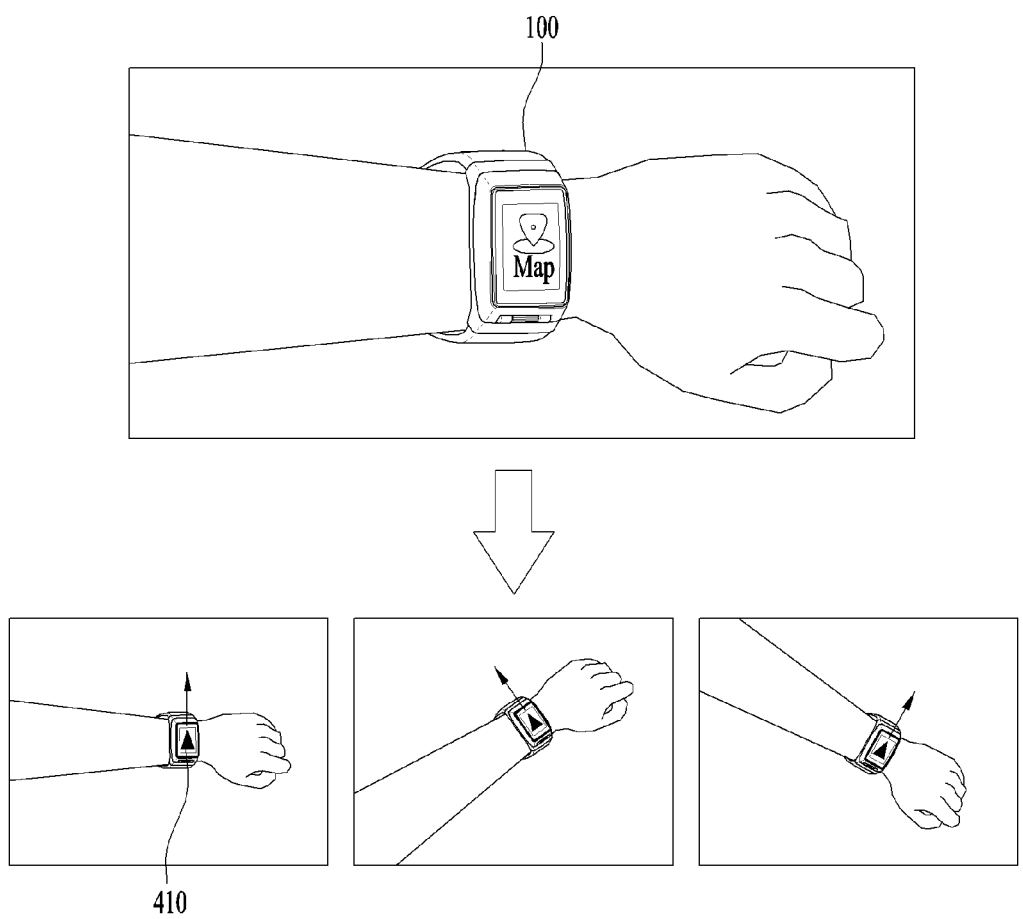
FIG. 5 is a diagram of a method for a portable device to display a first object based on a predetermined direction according to one embodiment of the present specification.

FIG. 5 is a diagram of a method for a portable device to display a first object based on a predetermined direction according to one embodiment of the present specification. A foot wearable device 200 may detect whether the foot wearable device 200 is worn using a wearing sensor unit 270. In this case, if the foot wearable device 200 detects that the foot wearable device 200 is worn, the foot wearable device may transmit a triggering signal indicating the wearing of the foot wearable device to a portable device 100.

As an example, if the portable device 100 receives the triggering signal indicating the wearing of the foot wearable device 200, the portable device may display a first application. In this case, as mentioned in the foregoing description, the first object may be displayed based on a front direction of the foot wearable device 200. And, a second object may be displayed based on a front direction of the portable device 100. In this case, as an example, the foot wearable device 200 may detect that the wearing of the foot wearable device 200 is released. In this case, the foot wearable device 200 may transmit a triggering signal indicating the release of the wearing of the foot wearable device 200 to the portable device 100. In particular, the portable device 100 may detect the release of the wearing of the foot wearable device 200 while displaying the first application. In this case, the portable device 100 may display the first object and the second object based on a second direction. In particular, if the foot wearable device is not worn, the portable device may display the first object based on the front direction of the portable device 100.

As a different example, if the foot wearable device 200 is not worn, the portable device 100 may differently configure a method of displaying the first object and the second object. More specifically, the first object may be displayed based on the front direction of the portable device 100 at the outside of the portable device 100. In this case, the first object may be displayed based on bearing information of a real space. And, the second object may be displayed based on the front direction of the portable device at the inside of the portable device 100. In this case, the front direction may correspond to a direction in which visual information is displayed. In particular, the second object may be displayed based on a reference direction of the inside of the portable device 100 instead of the bearing information of the real space.

FIG. 6 is a diagram of a method for a portable device to display a first object based on a front direction of a foot wearable device according to one embodiment of the present specification. The foot wearable device 200 may detect that the foot wearable device is worn by a user using a wearing sensor unit 270. In this case, the foot wearable device 200 may transmit a triggering signal indicating wearing of the foot wearable device to the portable device 100. In this case, the portable device 100 may display a first object 410 based on the received first triggering signal. In this case, as an example, if a front direction of the foot wearable device corresponds to a first direction, the foot wearable device 200 may transmit the first triggering signal to the portable device 100. In this case, the portable device 100 may display the first object 410 based on the first direction.

In this case, referring to FIG. 6, the portable device may display the first object 410 based on the first direction irrespective of the front direction of the portable device 100. More specifically, a user may wear the portable device 100 corresponding to a wearable device 100. In this case, if the user moves arms of the user back and forth, the front direction of the portable device may change. In this case, visual information displayed on the portable device 100 may be displayed according to a direction of the portable device 100. In this case, as an example, the first object 410 may be displayed irrespective of whether the front direction of the portable device 100 changes. In particular, the first object 410 may be consistently displayed based on the first direction as long as the direction of the foot wearable device 200 is not changed.

FIGS. 7a and 7b are diagrams of a method for a portable device to display a first application including a first object and a second object according to one embodiment of the present specification. If a foot wearable device 200 detects that a front direction corresponds to a first direction, the foot wearable device may transmit a first triggering signal to the portable device 100. And, the portable device 100 may detect that a front direction of the portable device 100 corresponds to a second direction. In this case, the portable device 100 may display a first object 410 based on the first direction based on the first triggering signal. And, the portable device 100 may display a second object 710 based on the second direction based on the detected front direction. In this case, as an example, if the front direction is changed to a third direction from the first direction, the foot wearable device 200 may transmit a second triggering signal to the portable device 100. In this case, the portable device 100 may display the first object 410 based on the changed third direction. In this case, the portable device 100 may display the second object 710 based on the second direction. In particular, the portable device 100 may display the first object 410 only based on the front direction of the foot wearable device 200. As a different example, the portable device 100 may detect that the front direction of the portable device 100 is changed to the third direction from the second direction. In this case, as an example, the portable device 100 may display the second object 710 based on the changed third direction. In this case, the portable device 100 may display the first object 410 based on the first direction. In particular, the portable device 100 may display the second object 710 only based on the front direction of the portable device 100.

As an example, referring to FIG. 7a, the portable device 100 may display a first object 410 and a second object 710 irrespective of the front direction of the foot wearable device 200. In this case, as an example, the first object 410 may correspond to an object indicating current location information and direction information of the portable device 100. And, the second object 710 may correspond to an object indicating surrounding situation information based on the current location information of the portable device 100. As an example, the second object 710 may correspond to an object indicating information on a building, a road and the like in a map application. The second object may correspond to a plurality of objects. In this case, the portable device 100 may display the first object 410 and the second object 710 based on the front direction of the portable device 100. In this case, as an example, a method of displaying the first object 410 and a method of displaying the second object 710 may be different from each other. As an example, the portable device 100 may display the first object 410 based on bearing information of a real space using the front direction of the portable device 100. In particular, the portable device 100 may display the first object based on the bearing to which the front direction of the portable device is heading at the outside of the portable device 100. And, the portable device 100 may display the second object 710 based on the front direction at the inside of the portable device 100. In particular, the second object 710 may be displayed at the inside of the portable device 100 based on a direction which is displayed when a user faces the front direction. In this case, as an example, the portable device 100 may display a first application corresponding to a map application. In this case, the portable device may display the second object 710 corresponding to information on surrounding buildings and roads. And, the portable device 100 may display the first object 410 corresponding to current location information and direction information. In this case, the portable device 100 may display the first object 410 in a bearing to which the front direction is heading at the outside of the portable device 100. In this case, a direction to which the first object 410 is heading may correspond to a direction to which a road is heading on the map application. In this case, as an example, the front direction of the portable device 100 may change. In this case, the portable device 100 may change the direction of the first object 410 based on the changed direction. In this case, since the second object 710 is displayed based on the front direction at the inside of the portable device 100, the second object may be displayed in an identical form. In this case, the bearing to which the first object 410 is heading may be different from the direction to which the road is heading on the map application. In particular, if the front direction of the portable device 100 changes, the second object 710 is displayed in an identical form and the first object 410 may be displayed in a manner of being changed based on a bearing of a real space. In this case, a user may have inconvenience in that the user should use the map application in a manner of changing the front direction of the portable device 100 to make the inside and the outside to be identical to each other.

In this case, referring to FIG. 7b, the portable device 100 may display the first object 410 based on a front direction of the foot wearable device 200. And, the portable device 100 may display the second object 710 based on the front direction of the portable device 100. In this case, as mentioned in the foregoing description, the portable device 100 may display the second object 710 based on the front direction of the inside of the portable device. In this case, as an example, the front direction of the foot wearable device 200 may correspond to a first direction. In this case, the first direction may correspond to a direction to which a road is heading on the map application. In this case, the front direction of the portable device 100 may correspond to a second direction. In this case, the second direction may be configured based on a direction of a user gazing at the portable device 100. In this case, as an example, the second direction may be changed to a third direction. In particular, the front direction of the portable device may change. In this case, as mentioned in the foregoing description, the second object 710 may be displayed in an identical form. And, the portable device 100 may maintain the first object in the identical first direction. In particular, if the front direction of the foot wearable device 200 is not changed from the direction to which the road is heading, the portable device 100 may maintain the direction to which the first object 410 is heading on the map application although the front direction of the portable device 100 is changed. By doing so, a user may check a moving direction irrespective of movement of the portable device 100.

FIG. 8 is a diagram of a method for a portable device to provide feedback based on path information according to one embodiment of the present specification. When a portable device 100 displays a first application, the portable device 100 may further display a first interface 810 indicating path information. In this case, as an example, the first application may correspond to a map application. In this case, as an example, the first interface 810 may correspond to path information predetermined by a user or a processor 170. And, as an example, the portable device 100 may further display a first indicator 820 indicating a path moving direction based on location information of the portable device 100 in the first interface 810. By doing so, a user is able to know a direction heading to a destination. In this case, as an example, if a front direction of a foot wearable device 200 corresponds to a first direction, the portable device 100 may display a first object 410 based on the first direction. In this case, as an example, if the path moving direction of the first interface and the first direction are not identical to each other, the portable device 100 may provide feedback. In this case, as an example, the feedback may include at least one selected from the group consisting of audio feedback, visual feedback and tactile feedback. In particular, if a user moves to a direction different from a direction of a destination based on the front direction of the foot wearable device 200, the portable device 100 may provide feedback to the user. By doing so, the user may determine whether the user is moving according to a path based on the front direction of the foot wearable device 200.

As a different example, the foot wearable device 200 may detect surrounding topographic information of the foot wearable device 200 based on the front direction. In this case, as an example, the foot wearable device 200 may detect the surrounding topographic information using a camera unit 230. In this case, the foot wearable device 200 may transmit the surrounding topographic information to the portable device 100. In this case, as an example, the portable device 100 may change path information of the first interface 810 based on the received surrounding topographic information. As an example, if there exists an obstruction, the portable device 100 may change the path information of the first interface 810 based on the received surrounding topographic information. By doing so, a user may accept guidance of a safe road heading to a destination.

As a further different example, the portable device 100 may store history information on a moving path in a state that the foot wearable device 200 and the portable device 100 are worn. In this case, as an example, the portable device 100 may periodically receive information on a front direction from the foot wearable device 200. The portable device 100 may store the history information on the moving path based on the front direction information received from the foot wearable device 200. By doing so, a user may check information on movement while wearing the foot wearable device 200.

Figure 9:
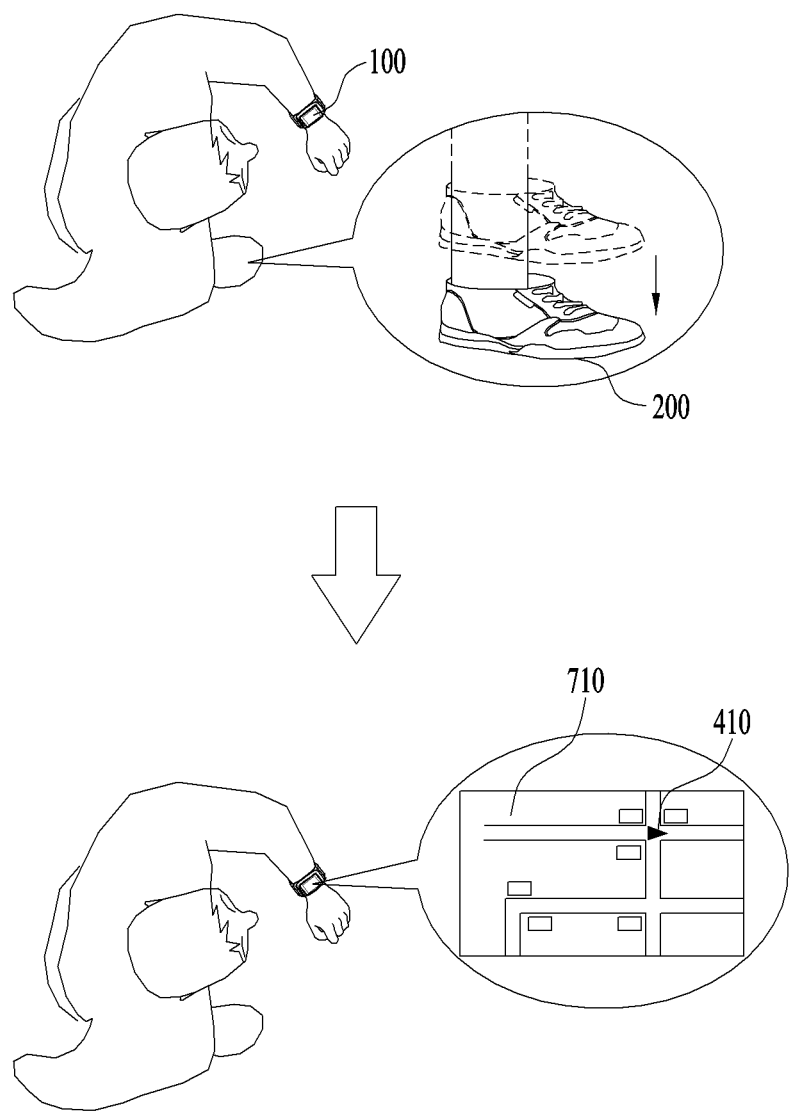
FIG. 9 is a diagram of a method for a portable device to display a first application according to one embodiment of the present specification.

FIG. 9 is a diagram of a method for a portable device to display a first application according to one embodiment of the present specification. A foot wearable device 200 may detect a control input of a user. In this case, as an example, the foot wearable device 200 may further include a control input sensing unit (not depicted). The foot wearable device 200 may detect the control input of the user using the control input sensing unit. In this case, as an example, a control input may correspond to an input detected by an action of stamping a foot of the user. More specifically, as an example, the foot wearable device 200 may further include a sensor (not depicted) capable of measuring pressure. In this case, the foot wearable device 200 may detect that a value of the pressure is changed to a value greater than a predetermined value. In this case, the foot wearable device 200 may detect a control input. And, the foot wearable device 200 may detect a control input in various ways, by which the present specification may be non-limited. If the foot wearable device 200 detects a control input, the foot wearable device 200 may transmit a triggering signal to the portable device 100 in response to the control input. In this case, having received the triggering signal, the portable device 100 may display a first application. In particular, the portable device 100 may display the first application based on the triggering signal received from the foot wearable device 200. By doing so, a user may execute an application of the portable device 100 via the foot wearable device 200.

Figure 10:
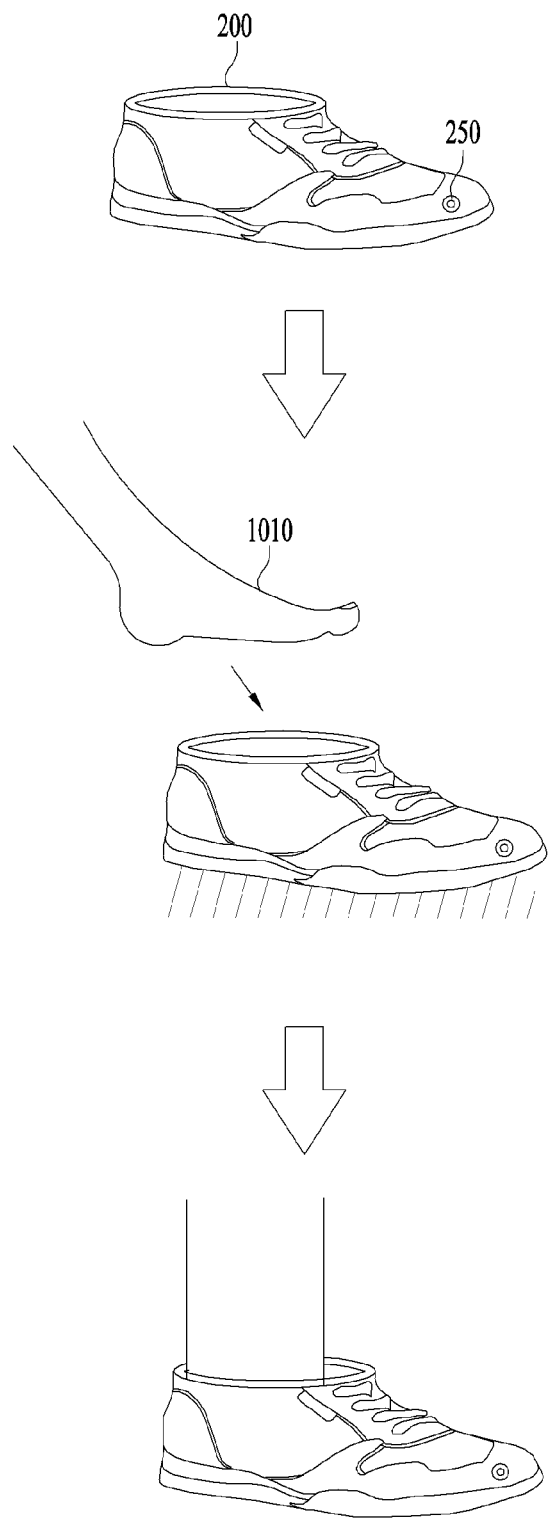
FIG. 10 is a diagram of a method for a foot wearable device to radiate a light source in a system including a wearable device according to one embodiment of the present specification.

FIG. 10 is a diagram of a method for a foot wearable device to radiate a light source in a system including a wearable device according to one embodiment of the present specification. A foot wearable device 200 may measure surrounding illumination of the foot wearable device using an illumination sensing unit 250. In this case, as an example, there may exist a part where illumination is less than a predetermined value near the foot wearable device 200. As an example, a part near the foot wearable device 200 may be dark. In this case, the foot wearable device 200 may detect that a foot 1010 of a user is entering within a predetermined distance using a sensor unit (not depicted). As an example, the foot wearable device 200 may detect that the foot 1010 of the user is positioned within the predetermined distance using a proximity sensor. And, the foot wearable device 200 may detect that the foot 1010 of the user is entering within the predetermined distance in various ways, by which the present specification may be non-limited. In this case, as an example, the predetermined distance may correspond to a threshold distance and may have a prescribed error. In this case, the foot wearable device 200 may further include a light source unit (not depicted). In this case, the light source (not depicted) may correspond to a unit configured to emit light. If the foot wearable device 200 detects that the foot 1010 of the user is positioned within the predetermined distance, the foot wearable device 200 may illuminate via the light source unit. In particular, if the foot 1010 of the user is getting closer, the foot wearable device 200 may deliver location information of the foot wearable device 200 by emitting light. In this case, as an example, the portable device 100 may further display visual information indicating that the foot 1010 of the user is positioned adjacent to the foot wearable device 200. And, the foot wearable device 200 may detect that the foot wearable device 200 is worn using a wearing sensor unit 270. In this case, the foot wearable device 200 may control the light source unit not to emit light. By doing so, the user may easily find and wear the foot wearable device 200 in a state that surrounding of the user is dark.

FIG. 11 is a diagram for a method of interlocking a foot wearable device and a portable device in a system including a wearable device according to one embodiment of the present specification. A foot wearable device 200 may detect that the foot wearable device is worn by a user using a wearing sensor unit 270. In this case, as an example, when the foot wearable device 200 worn on the user is detected, the foot wearable device 200 may detect status information of the user. More specifically, the foot wearable device 200 may determine the status information of the user using a foot of the user while being worn on the user. In this case, as an example, the status information may correspond to weight, pulse information, body condition information and the like. And, the status information corresponds to information capable of being detected by a sensor unit (not depicted), by which the present specification may be non-limited. In this case, the portable device 100 may receive the status information of the user from the foot wearable device 200. In this case, the portable device 100 may display the status information of the user. By doing so, the user may frequently check the status information of the user by wearing the foot wearable device 200.

Figure 12B:
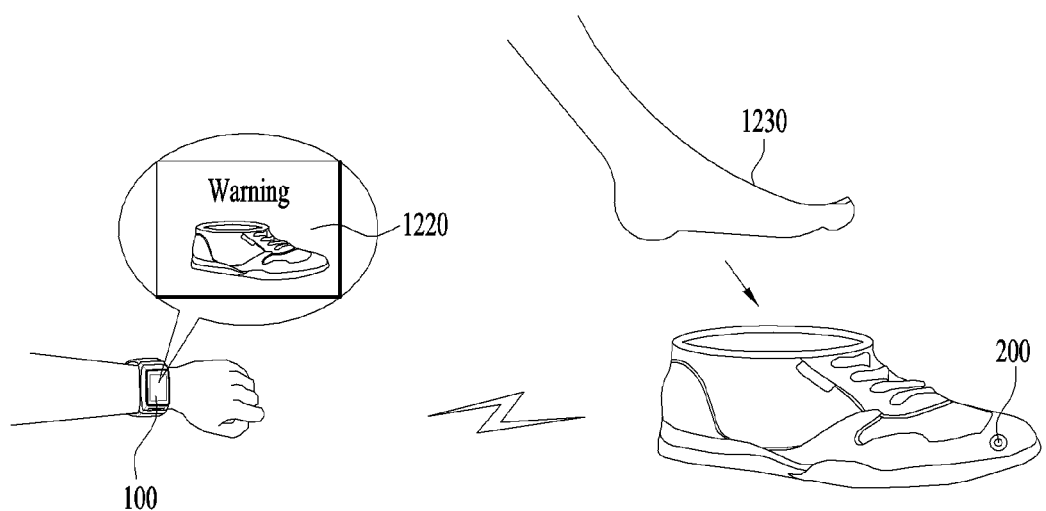

FIGS. 12a and 12b are diagrams for a method of interlocking a foot wearable device and a portable device in a system including a wearable device according to one embodiment of the present specification.

In this case, referring to FIG. 12a, a foot wearable device 200 may execute a security mode. In this case, the security mode may correspond to a mode determining whether the foot wearable device is worn by a predetermined user. More specifically, the foot wearable device 200 may detect pattern information in a state of being worn by a user. In this case, as an example, the foot wearable device 200 may detect movement of the foot wearable device 200 worn on a foot of a user using a motion sensing unit 260. In this case, as an example, the pattern information may correspond to information of the foot wearable device moving to a predetermined direction. If the foot wearable device 200 detects predetermined pattern information, the foot wearable device 200 may execute a security mode. In this case, as an example, the portable device 100 may receive information on the security mode from the foot wearable device 200. The portable device 100 may display the received information on the security mode.

And, as an example, referring to FIG. 12b, if the security mode is set, the foot wearable device 200 may detect that the foot wearable device is worn on a different user instead of a predetermined user. In this case, the foot wearable device 200 may transmit information on whether the foot wearable device 200 is worn on the different user to the portable device 100. In this case, the portable device 100 may provide the information on whether the foot wearable device is worn on the different user by feedback. In this case, as an example, the feedback may include at least one selected from the group consisting of audio feedback, visual feedback and tactile feedback. As a different example, the portable device may detect that the foot wearable device 200 is positioned at a distance more than a predetermined distance from the portable device 100. In this case, the portable device may provide feedback to a user. In particular, the security mode may correspond to a mode checking whether the foot wearable device 200 is worn on the different user instead of the predetermined user, by which the present specification may be non-limited. By doing so, a user may prevent the foot wearable device from being stolen by a different user when the user is not wearing the foot wearable device 200.

Figure 13:
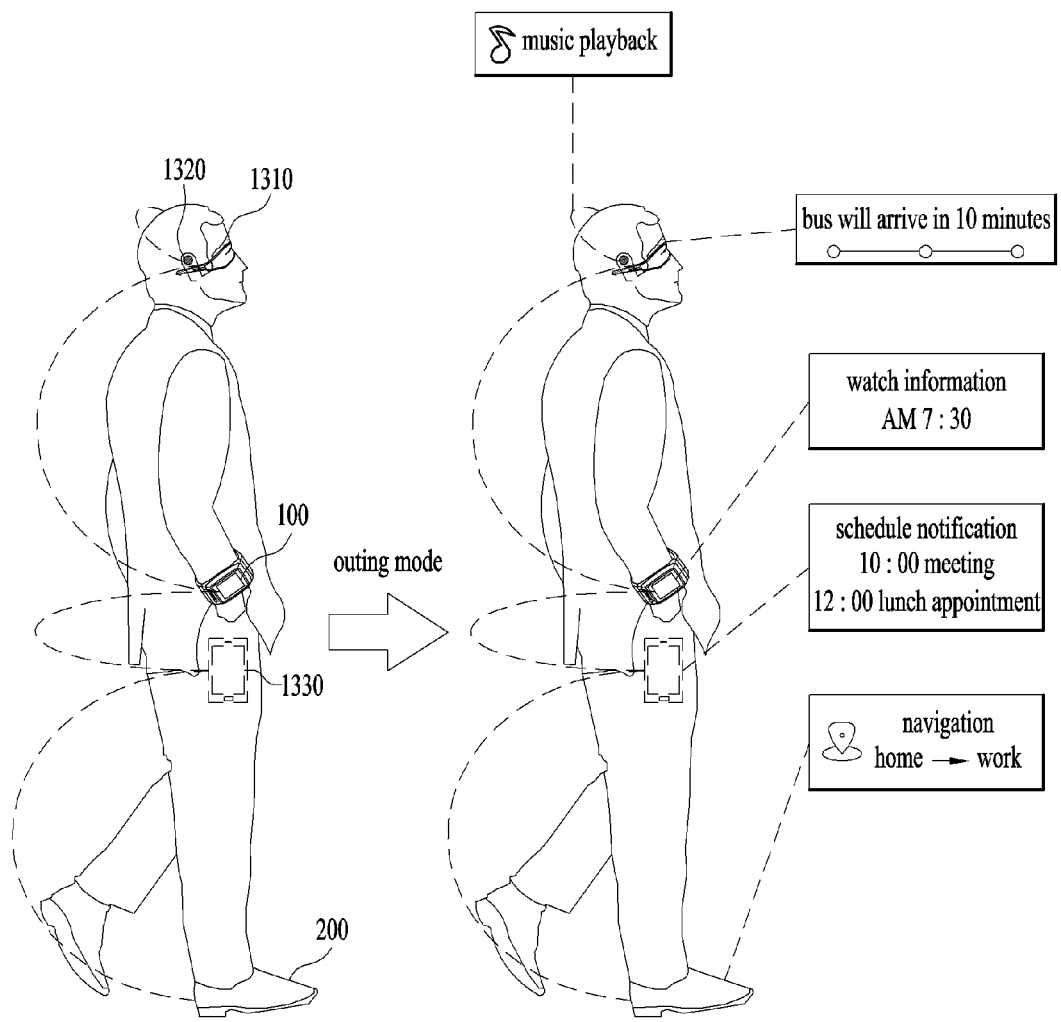
FIG. 13 is a diagram for a method of interlocking a wearable device and a portable device in a system including the wearable device according to one embodiment of the present specification.

FIG. 13 is a diagram for a method of interlocking a wearable device and a portable device in a system including the wearable device according to one embodiment of the present specification. The portable device 100 and the foot wearable device 200 may correspond to a single system. In this case, as an example, the system may further include different devices 1310/1320/1330. In this case, as an example, the system may include a HMD device 1310. As a different example, the system may further include an earphone 1320. As a further different example, the system may further include a smartphone 1330. In particular, the system may include a plurality of devices used by a user, by which the present specification may be non-limited. In this case, as an example, if an outing mode is set to the system, each of a plurality of the devices 100/200/1310/1320/1330 may execute an operation.

As an example, if the outing mode is set to the system, the HMD device 1310 may display information on a bus frequently used by a user. And, the earphone 1320 may continuously display music most recently played. And, a smart watch corresponding to the portable device 100 may display watch information. And, the smartphone may display daily schedule information. And, the foot wearable device 200 may execute a navigation function. In particular, when the system is changed to the outing mode, each of a plurality of the devices 100/200/1310/1320/1330 included in the system may execute a predetermined operation.

In this case, as an example, the system may set the outing mode based on the foot wearable device 200. More specifically, if the system detects that the foot wearable device 200 is worn, the system may execute the outing mode. In this case, as an example, when a user is going out, the user may lastly wear the foot wearable device 200. Hence, the system may set the outing mode based on the foot wearable device 200. In particular, wearing the foot wearable device 200 may correspond to a triggering signal for executing the outing mode. By doing so, the user may control a plurality of the devices without any separate control input.

Figure 14:
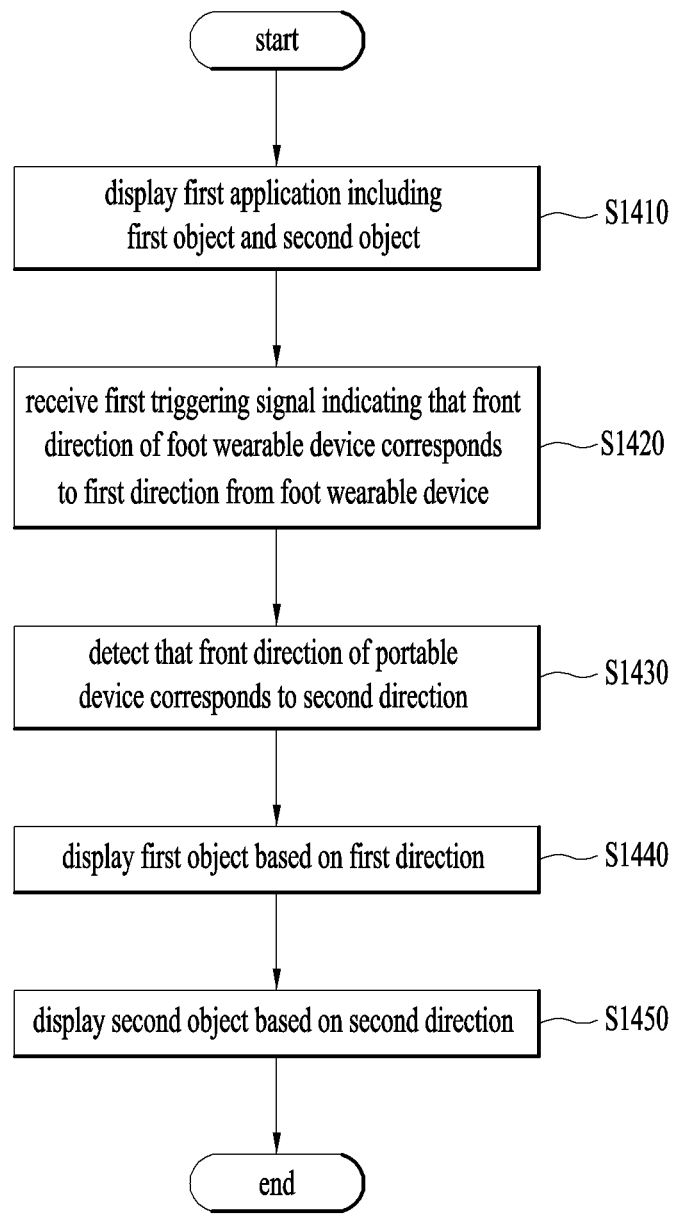
FIG. 14 is a flowchart for a method of controlling a portable device according to one embodiment of the present specification.

FIG. 14 is a flowchart for a method of controlling a portable device according to one embodiment of the present specification. A portable device 100 may display a first application including a first object and a second object [S1410]. In this case, as mentioned earlier in FIG. 1, the first object may correspond to an object indicating current location information and direction information of the portable device 100. And, the second object may correspond to an object indicating surrounding information based on the current location information of the portable device 100. In this case, as an example, the second object may correspond to a building, a road or the like.

Subsequently, the portable device may receive a first triggering signal indicating that a front direction of a foot wearable device corresponds a first direction from the foot wearable device [S1420]. In this case, as mentioned earlier in FIG. 1, the foot wearable device 200 may transmit information on the front direction of the foot wearable device 200 to the portable device 100 via a communication unit. In this case, the information on the front direction of the foot wearable device 200 may be identical to a moving direction of a user. In particular, the portable device 100 may check information on the moving direction of the user by receiving the information on the front direction of the foot wearable device 200.

Subsequently, the portable device 100 may detect that a front direction of the portable device 100 corresponds to a second direction [S1430]. In this case, as mentioned earlier in FIG. 1, as an example, the front direction of the portable device 100 may correspond to a direction in which visual information is displayed. More specifically, a processor 170 may display the visual information based on the front direction of the portable device 100. As an example, the processor 170 may display the visual information in a portrait mode or a landscape mode. In this case, the portrait mode may correspond to a state that the portable device 100 stands. In this case, as an example, the front direction of the portable device 100 may correspond to an up direction of the standing portable device 100. And, the landscape mode may correspond to a state that the portable device 100 is laid. In this case, as an example, the front direction of the portable device 100 may correspond to an up direction of the laid portable device. In particular, the front direction of the portable device 100 may correspond to a reference direction in which the visual information is displayed.

Subsequently, the portable device 100 may display the first object based on the first direction [S1440]. In this case, as mentioned earlier in FIG. 7b, the portable device 100 may display the first object based on the front direction of the foot wearable device 200. In this case, if the front direction of the foot wearable device 200 changes, the portable device 100 may display the first object based on the changed front direction of the foot wearable device 200. In particular, the first object may correspond to an object which is differently displayed according to the front direction of the foot wearable device 200 only.

Subsequently, the portable device 100 may display the second object based on the second direction [S1450]. In this case, as mentioned earlier in FIG. 7b, the portable device 100 may display the second object based on the front direction of the portable device 100. In this case, as mentioned in the foregoing description, the second object may correspond to an object which is displayed based on a direction in which the visual information is displayed in the inside of the portable device 100. In particular, the second object may correspond to visual information displayed in a prescribed direction in the inside of the portable device 100. In this case, as an example, if the front direction of the portable device 100 changes, the portable device 100 may display the second object based on the changed front direction. In particular, the second object may correspond to an object which is differently displayed according to the front direction of the portable device 100 only.

For clarity of explanation, each diagram is explained in a manner of being divided. Yet, it is possible to design a new embodiment to implement the new embodiment by combining the embodiments, which are described in each of the diagrams. And, according to the necessity of those skilled in the art, designing a recording media readable by the computer, which has recorded a program for executing the previously explained embodiments, also belongs to a scope of a right.

A portable device 100 according to the present specification and a method of controlling therefor may not limitedly apply to the composition and method of the aforementioned embodiments. The aforementioned embodiments may be configured in a manner of being selectively combined the whole of the embodiments or a part of the embodiments to achieve various modifications.

Meanwhile, a portable device 100 according to the present specification and a method of controlling therefor may be implemented with a code readable by a processor in a recording media readable by the processor, which is equipped in a network device. The recording media readable by the processor may include all kinds of recording devices for storing data capable of being read by the processor. The examples of the recording media readable by the processor may include a ROM, a RAM, a magnetic tape, a floppy disc, an optical data storing device and the like. And, implementing in a form of a carrier wave such as a transmission via the internet and the like is also included. And, since the recording media readable by the processor are distributed to the computers connected by a network, codes readable by the processor may be stored and executed in a manner of being distributed.

While the present specification has been described and illustrated herein with reference to the preferred embodiments and diagrams thereof, the present specification may be non-limited to the aforementioned embodiments and it will be apparent to those skilled in the art that various modifications and variations may be made therein without departing from the spirit and scope of the present specification. Thus, it is intended that the present specification covers the modifications and variations of this invention that come within the scope of the appended claims and their equivalents.

And, both an apparatus invention and a method invention are explained in the present specification and the explanation on both of the inventions may be complementally applied, if necessary.

What is claimed is:
1. A portable device, comprising:
a display unit configured to display visual information;
a location information sensing unit configured to detect location information of the portable device;
a direction information sensing unit configured to detect direction information of the portable device;
a communication unit configured to receive information from a foot wearable device; and
a processor configured to:
display a first application including a first object and a second object,
display the first object based on a first direction and the second object based on a second direction when a first triggering signal indicating that a front direction of the foot wearable device corresponds to the first direction is received from the foot wearable device and a front direction of the portable device is detected as the second direction,
display a first interface indicating path information when the first application is displayed,
display a first indicator indicating a path moving direction in the first interface based on the location information of the portable device, and
provide at least one of audio feedback and tactile feedback when the path moving direction of the first indicator is not identical to the first direction.

2. The portable device of claim 1, wherein the processor is further configured to:
display the first object based on changed a third direction and the second object based on the second direction when a second triggering signal indicating that the front direction of the foot wearable device is changed to the third direction from the first direction is received from the foot wearable device.

3. The portable device of claim 1, wherein the processor is further configured to:
display the first object based on the first direction and the second object based on changed a third direction when the front direction of the portable device is changed to the third direction from the second direction.

4. The portable device of claim 1, wherein the first object corresponds to an object indicating current location information of the portable device.

5. The portable device of claim 4, wherein the second object corresponds to an object indicating information on a real object positioned adjacent to the portable device based on the current location information of the portable device.

6. The portable device of claim 1, wherein the foot wearable device detects surrounding topographic information of the foot wearable device based on the front direction and transmits the detected surrounding topographic information to the portable device.

7. The portable device of claim 6, wherein the processor is further configured to:
receive the surrounding topographic information from the foot wearable device, and
set the path information of the first interface based on the received surrounding topographic information.

8. The portable device of claim 1, wherein the processor is further configured to display the first application when a second triggering signal is received from the foot wearable device.

9. The portable device of claim 8, wherein the foot wearable transmits the second triggering signal to the portable device when a control input of a user is detected.

10. The portable device of claim 1, wherein the processor is further configured to display the first object and the second object based on the second direction when a second triggering signal indicating release of wearing of the foot wearable device is received in a state that the first application is displayed.

11. The portable device of claim 1, further comprising a storage unit configured to store information,
wherein the processor is further configured to store history information on a moving path based on the front direction of the foot wearable device when the foot wearable device and the portable device are moving in a state of being worn.

12. A method of controlling a portable device, the method comprising:
displaying, via a display unit, a first application including a first object and a second object;
receiving, via a communication unit, from a foot wearable device a first triggering signal indicating that a front direction of the foot wearable device corresponds to a first direction;
detecting, via a direction information sensing unit, a front direction of the portable device corresponding to a second direction;
displaying, via the display unit;
displaying, via the display unit, the second object based on the second direction;
displaying a first interface indicating path information when the first application is displayed;
displaying a first indicator indicating a path moving direction in the first interface based on the location information of the portable device; and
providing at least one of audio feedback and tactile feedback when the path moving direction of the first indicator is not identical to the first direction.

13. The method of claim 12, further comprising:
receiving a second triggering signal indicating that the front direction of the foot wearable device is changed to a third direction from the first direction from the foot wearable device; and
displaying, via the display unit, the first object based on the changed third direction and displaying the second object based on the second direction.

14. The method of claim 12, further comprising:
detecting a change of the front direction of the portable device changed to a third direction from the second direction; and
displaying, via the display unit, the first object based on the first direction and displaying the second object based on the changed third direction.

* * * * *